United States Patent

Ochiai et al.

[11] Patent Number: 5,587,155
[45] Date of Patent: Dec. 24, 1996

[54] HAIR COSMETIC COMPOSITION

[75] Inventors: Ryuji Ochiai, Ichikawa; Kouzi Morita, Mitaka; Kazuyuki Yahagi, Tokyo, all of Japan

[73] Assignee: Kao Corporation, Tokyo, Japan

[21] Appl. No.: 367,228

[22] PCT Filed: Jul. 14, 1993

[86] PCT No.: PCT/JP93/00980

§ 371 Date: Jan. 18, 1995

§ 102(e) Date: Jan. 18, 1995

[87] PCT Pub. No.: WO94/02111

PCT Pub. Date: Feb. 3, 1994

[30] Foreign Application Priority Data

Jul. 21, 1992 [JP] Japan .................................. 4-194122
Feb. 9, 1993 [JP] Japan .................................. 5-021456

[51] Int. Cl.⁶ .................................. A61K 7/06; A61K 7/00
[52] U.S. Cl. .................................. 424/70.28; 424/70.1
[58] Field of Search .................................. 424/70.27, 70.28, 424/70.1

[56] References Cited

U.S. PATENT DOCUMENTS

| | | | |
|---|---|---|---|
| 4,534,877 | 8/1985 | Russell et al. | 252/106 |
| 4,613,622 | 9/1986 | Moeller et al. | 514/718 |
| 5,145,607 | 9/1992 | Rich | 252/547 |
| 5,211,942 | 5/1993 | Deppert et al. | 424/70 |
| 5,403,517 | 4/1995 | Horinishi et al. | 252/551 |

Primary Examiner—Sallie M. Gardner
Attorney, Agent, or Firm—Oblon, Spivak, McClelland, Maier & Neustadt, P.C.

[57] ABSTRACT

A hair cosmetic composition including (a) at least one compound selected from fatty acids containing a linear or branched alkyl or alkenyl group having 12–40 carbon atoms, salts thereof and fatty acid esters composed of one of the fatty acids and a polyhydric alcohol; (b) at least one aromatic alcohol represented by the general formula (1):

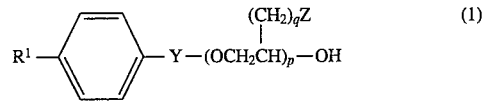

wherein $R^1$ means a hydrogen atom or a methyl or methoxy group, Y denotes a single bond or a linear or branched alkylene or alkenylene group having 1–3 carbon atoms, Z is a hydrogen atom or a hydroxyl group, and p and q stand individually for a number of 0–5; and (c) at least one cationic surfactant. The hair cosmetic composition has neither sticky nor oily feel to the touch, is excellent in hair-conditioning effects of, for example, giving users a moistured feel of the hair and imparting softness and smoothness to the hair, gives resilience to the hair and is superb in effects of preventing damage to the hair and of keeping the waves or curls of the hair beautiful.

5 Claims, No Drawings

HAIR COSMETIC COMPOSITION

TECHNICAL FIELD

The present invention relates to hair cosmetic compositions, and more specifically to hair cosmetic compositions which are excellent in hair-conditioning effects, and also can impart resilience to the hair and are superb in effects of preventing damage to the hair and of keeping the waves or curls of the hair beautiful.

BACKGROUND ART

In the conventional hair cosmetic compositions, a cationic surfactant such as a linear mono- or di-long-chain alkyl quaternary ammonium salt or branched mono- or di-long-chain alkyl quaternary ammonium salt has been incorporated with a view toward making the feel of the hair to the touch better, and an oil or fat such as a higher alcohol, glyceride or liquid paraffin has been used in combination with such a cationic surfactant to make the feel of the hair to the touch still better.

On the other hand, as methods of imparting resilience to the hair, there have been known, for example, a method in which a high-molecular weight substance is added to a hair cosmetic composition to cause the high-molecular weight substance to be adsorbed on the surface of the hair, thereby imparting resilience to the hair; and a method in which an astringent is incorporated into a hair cosmetic composition to astringe the hair.

However, these conventional hair cosmetic compositions have involved a drawback that the feel of the hair to the touch, i.e., softness, a moistured feel, smoothness and an antistat effect, which are hair-conditioning effects brought about thereby, are insufficient. With respect to the moistured feel of the hair, therefore, a measure to use an oil or fat in combination to make up for its deficiency has been taken. However, this measure has been accompanied by sticky and oily feel to the touch, and particularly still involved a problem that the hair-conditioning effects are insufficient for the damaged hair in a dry state. The conventional hair cosmetic compositions have also been insufficient in effects of preventing damage to the hair and of keeping the waves or curls of the hair beautiful. In addition, it has been impossible to improve the resilience of the hair while exhibiting these effects.

Therefore, there has been a demand for the development of a hair cosmetic composition which has neither sticky nor oily feel to the touch, is excellent in hair-conditioning effects of, for example, giving users a moistured feel, recovers resilience and is sufficient in effects of preventing damage to the hair and of keeping the waves or curls of the hair beautiful.

In view of the foregoing circumstances, the present inventors have carried out an extensive investigation. As a result, it has been found that the combined use of a cationic surfactant, a specific fatty acid, or a salt or ester thereof and an aromatic alcohol can provide a hair cosmetic composition in which the fatty acid, or the salt or ester thereof can permeate the hair so as not only to prevent damage to the hair upon washing or brushing of the hair, but also to impart resilience to the hair even in a dry state, and which exhibits excellent hair-conditioning effects of, for example, giving users a moistured feel and making the hair soft and smooth, and also has superb effects of keeping the waves or curls of the hair beautiful, leading to completion of the present invention.

DISCLOSURE OF THE INVENTION

According to the present invention, there is provided a hair cosmetic composition comprising the following components (a), (b) and (c):

(a) at least one compound selected from fatty acids containing a linear or branched alkyl or alkenyl group having 12–40 carbon atoms, salts thereof and fatty acid esters composed of one of the fatty acids and a polyhydric alcohol;

(b) at least one aromatic alcohol represented by the general formula (1):

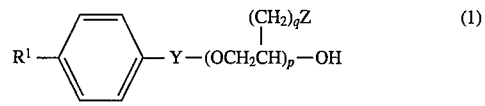

wherein $R^1$ means a hydrogen atom or a methyl or methoxy group, Y denotes a single bond or a linear or branched alkylene or alkenylene group having 1–3 carbon atoms, Z is a hydrogen atom or a hydroxyl group, and p and q stand individually for a number of 0–5; and (c) at least one cationic surfactant.

BEST MODE FOR CARRYING OUT THE INVENTION

The fatty acid of the component (a) useful in the practice of the present invention contains a linear or branched alkyl or alkenyl group having 12–40 carbon atoms. Examples thereof include lauric acid, tridecanoic acid, myristic acid, pentadecanoic acid, palmitic acid, heptadecanoic acid, stearic acid, nonadecanoic acid, icosanoic acid, heneicosanoic acid, behenic acid, lignoceric acid, cerotic acid, montanic acid, melissic acid, lacceric acid, geddic acid, lauroleic acid, myristoleic acid, palmitoleic acid, oleic acid, gadoleic acid, erucic acid, linoleic acid, linolenic acid, 2-heptylundecanoic acid, 2-isoheptylisoundecanoic acid, isostearic acid (for example, products of Emery Industries, Inc., and Union Camp Corp.), 18-methylicosanoic acid, 2-octylarachidic acid, 2-methylstearic acid, 2-decyldodecanoic acid, 2-dodecyltetradecaonic acid, 2-tetradecylhexadecanoic acid, 2-hexadecyloctadecanoic acid, 2-octadecylicosanoic acid, 3-pentyloctanoic acid, 3-heptyldecanoic acid, 3-nonyldodecanoic acid, 3-undecyltetradecanoic acid, 3-tridecylhexadecanoic acid, 2-octyldodecanoic acid, 2-pentylnonanoic acid, 2-hexyldecanoic acid and 12-hydroxystearic acid.

Of these fatty acids, those having 18–25 carbon atoms, in particular, icosanoic acid, heneicosanoic acid, behenic acid, lignoceric acid, 2-heptylundecanoic acid, 2-isoheptylisoundecanoic acid, isostearic acid, 18-methylicosanoic acid, 3-nonyldodecanoic acid, 3-undecyltetradecanoic acid, 2-methylstearic acid are preferred.

Examples of salts of these fatty acids include salts of alkali metals such as sodium, lithium and potassium, alkaline earth metals such as calcium and magnesium, organic amines such as ammonia, triethanolamine, diethanolamine and monoethanolamine, and basic amino acids such as lysine and arginine.

Examples of polyhydric alcohols constituting the fatty acid esters includes glycerol, diglycerol, triglycerol, tetraglycerol, polyglycerol (polymerization degree: 5 or higher), erythritol, pentaerythritol, sorbitol, maltitol, mannitol, sugaralcohols, ethylene glycol and propylene glycol.

The fatty acids, or the salts or esters thereof as the component (a), may be used either singly or in any combination thereof, and may preferably be incorporated in a proportion of 0.1–20 wt. % (hereinafter indicated merely by "%"), particularly 0.5–10.0% based on the whole hair cosmetic composition. Any proportions lower than 0.1% result in a composition which fails to exhibit sufficient effects. Any proportions exceeding 20% result in a composition having a sticky feel to the touch and hence giving users an unpleasant feel. It is hence not preferable to use the component (a) in any proportions outside the above range.

The aromatic alcohols of the component (b) are those represented by the general formula (1) and include, for example, benzyl alcohol, cinnamyl alcohol, phenethyl alcohol, p-anisyl alcohol, p-methylbenzyl alcohol, phenoxyethanol and 2-benzyloxyethanol. Of these, 2-benzyloxyethanol is particularly preferred.

These aromatic alcohols may be used either singly or in any combination thereof, and may preferably be incorporated in a proportion of 0.1–50%, particularly 1–30% based on the whole hair cosmetic composition. Any proportions lower than 0.1% result in a composition which fails to achieve the effects of the present invention. On the other hand, any proportions exceeding 50% result in a composition which tends to make the stability of the system deteriorated.

The hair cosmetic compositions according to the present invention may contain a lower alcohol and/or a lower polyol, which are used routinely with a view toward improving the solubility of these aromatic alcohols. Such lower alcohols include those having 1–5 carbon atoms, for example, ethanol, isopropanol, n-propanol, n-butanol and isobutanol. The lower polyols include those having 2–5 carbon atoms, for example, ethylene glycol, propylene glycol 1,3-butanediol and glycerol. These lower alcohols or lower polyols may preferably be incorporated in a proportion of 0.1–50%, particularly 1–35% based on the whole hair cosmetic composition.

No particular limitation is imposed on the cationic surfactant of the component (c) so long as it is in common use in hair cosmetic compositions. Examples thereof include quaternary ammonium salts represented by the following general formulae (2) and (3):

(2)

wherein at least one of $R^2$, $R^3$, $R^4$ and $R^5$ means an alkyl or alkenyl group which has 8–28 carbon atoms in total and may be substituted by an alkoxy, alkenyloxy, alkanoylamino or alkenoylamino group, the residual R groups denote individually a benzyl group, or an alkyl or hydroxyalkyl group having 1–5 carbon atoms, and $X^-$ stands for a halogen ion or an organic anion; and

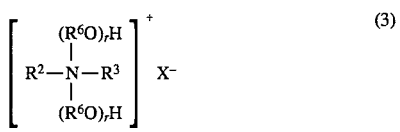

(3)

wherein at least one of $R^2$ and $R^3$ means an alkyl or alkenyl group which has 8–28 carbon atoms in total and may be substituted by an alkoxy, alkenyloxy, alkanoylamino or alkenoylamino group, the other group denotes a benzyl group, or an alkyl or hydroxyalkyl group having 1–5 carbon atoms, $R^6$ is an alkylene group having 2–3 carbon atoms, $X^-$ means a halogen ion or an organic anion, and r stands for an integer of 1–20.

Of these cationic surfactants, the quaternary ammonium salts represented by the general formula (2) are particularly preferred. Preferable examples of the compounds of the general formula (2) include branched quaternary ammonium salts represented by the following general formulae (4) through (6):

(4)

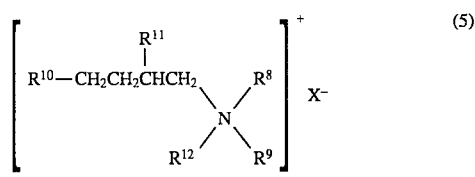

(5)

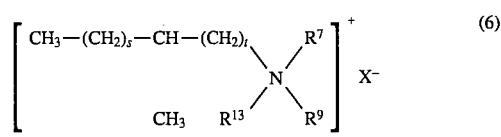

(6)

wherein $R^7$ means a mixture of (A) a branched alkyl group represented by

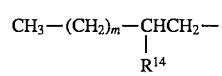

in which $R^{14}$ denotes a methyl or ethyl group, and m stands for such an integer that the total number of carbon atoms in the alkyl group falls within a range of 8–16, and (B) a linear alkyl group represented by $CH_3$—$(CH_2)n$— in which n stands for an integer of 7–15, with the proviso that the branching rate, (A)/(A)+(B) is 10–100%, $R^8$ and $R^9$ denote individually an alkyl or hydroxyalkyl group having 1–3 carbon atoms, $R^{10}$ and $R^{11}$ stand individually for an alkyl group having 2–12 carbon atoms, $R^{12}$ is a group,

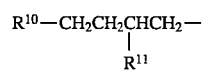

or an alkyl group having 1–3 carbon atoms, $R^{13}$ means a group,

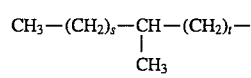

or an alkyl group having 1–3 carbon atoms, s stands for an integer of 2–14, t is an integer of 3–11, with the proviso that the sum of s and t is 9–21, and $X^-$ denotes a halogen ion or an organic anion.

Of these, the branched quaternary ammonium salts represented by the general formula (4) are generally synthesized, for example, by using an oxoalcohol having 8–16 carbon atoms as a starting material. Examples thereof include dialkyldimethylammonium salts, dialkylmethylhydroxyethylammonium salts and dialkylmethylbenzylammonium salts, which have alkyl groups derived from the oxoalcohol.

In the present invention, the quaternary ammonium salts in which the branching rate of $R^7$ in the formula (4) is 10–100% is generally used. However, those having a branching degree of 10–50% are particularly preferred. Besides, although the quaternary ammonium salts in which the total number of carbon atoms in $R^7$ is 8–16 are used, those having a fixed distribution of the number of carbon atoms are preferred, with those having a distribution described below being particularly preferred.

$C_8-C_{11}$: 5% or lower
$C_{12}$: 10–35%
$C_{13}$: 15–40%
$C_{14}$: 20–45%
$C_{15}$: 5–30%
$C_{16}$: 5% or lower.

Specific examples of such branched quaternary ammonium salts include dialkyldimethylammonium chlorides containing alkyl groups whose number of carbon atoms is 8–16 and whose branching rate is 10–50%.

On the other hand, the quaternary ammonium salts represented by the general formula (5) are generally synthesized by using, as a starting material, a Guerbet alcohol

having 8–28 carbon atoms.

Preferred examples of these quaternary ammonium salts include alkyltrimethylammonium salts, alkyldimethylbenzylammonium salts, dialkyldimethylammonium salts, dialkylmethylhydroxyethylammonium salts and dialkylmethylbenzylammonium salts, which have an alkyl group or alkyl groups derived from the Guerbet alcohol. Particularly preferred examples thereof include 2-decyltetradecyltrimethylammonium chloride, 2-dodecylhexadecyltrimethylammonium chloride, di-2-hexyldecyldimethylammonium chloride and di-2-octyldodecyldimethylammonium chloride.

Further, the methyl-branched quaternary ammonium salts represented by the general formula (6) are preferably those in which the sum of s and t is 15.

Specific examples of $X^-$ which are counter ions of the quaternary ammonium salts represented by the general formulae (2), (3), (4), (5) and (6) include halogen ions such as chlorine, iodine and bromine ions, and organic anions such as methosulfate, ethosulfate, methophosphate and ethophosphate anions.

These cationic surfactants of the component (c) may be used either singly or in any combination thereof, and may preferably be incorporated in a proportion of 0.01–20.0%, particularly 0.2–10.0% based on the whole hair cosmetic composition. Any proportions lower than 0.01% result in a composition which fails to achieve the effects of the present invention. On the other hand, any proportions exceeding 20% result in a composition having a sticky feel to the touch and hence giving users an unpleasant feel. It is hence not preferable to use the component (c) in any proportions outside the above range.

Incidentally, in the hair cosmetic compositions according to the present invention, optional ingredients, which are mixed routinely in hair cosmetic compositions, may be suitably incorporated in addition to the above-described essential ingredients, as necessary for the end application intended.

In the hair cosmetic compositions according to the present invention, for example, anionic surfactants such as alkylbenzene sulfonates, alkyl ether sulfates, olefin sulfonates, α-sulfo fatty acid esters, amino acid type surfactants, phosphate ester surfactants and sulfosuccinate ester surfactants; amphoteric surfactants such as sulfonic acid type surfactants, betaine type surfactants, alkylamine oxides and imidazoline type surfactants; and nonionic surfactants such as polyoxyethylene alkyl ethers, polyoxyethylene alkyl phenyl ethers, alkanolamides and alkylene oxide adducts thereof, sorbitan fatty acid esters, and alkylsaccharide surfactants may be used either singly or in any combination thereof according to the performance of various hair treatments intended. In particular, when the hair cosmetic composition of the present invention is provided as a shampoo, it is preferable to use the amino acid surfactant, phosphate ester surfactant, α-sulfo fatty acid ester, imidazoline type surfactant, alkylsaccharide surfactant and/or the like among the above-mentioned surfactants in due consideration of irritativeness to the skin and hair. In the hair cosmetic compositions according to the present invention, these surfactants may preferably be incorporated in a proportion of usually 0.01–40.0% in general. In particular, it is preferable to incorporate them in a proportion of 5–30.0% in the case where the hair cosmetic compositions are provided as detergents, or of 0.05–20.0% in the case where they are provided as hair cosmetic compositions other than the detergents.

In the hair cosmetic compositions according to the present invention, one or more of cationic polymers such as cationized cellulose derivatives, cationic starches, cationized guar gum derivatives, diallyl quaternary ammonium salt/acrylamide copolymers, quaternized polyvinyl pyrrolidone derivatives and polyglycol polyamine condensates may be incorporated with a view toward making the feel of the hair and skin to the tough better. Preferable specific examples of these cationic polymers include cationized celluloses having a molecular weight of about 100,000–3,000,000, cationized starches having a degree of cationization of about 0.01–1, cationized guar gums ("Jaguar", product of Celanese Corp., etc.) having a degree of cationization of about 0.01–1, diallyl quaternary ammonium salt/acrylamide copolymers having a molecular weight of about 30,000–2,000,000, quaternized polyvinyl pyrrolidone derivatives having a molecular weight of 10,000–2,000,000 and a cationic nitrogen content in the vinyl polymer of 0.004–0.2%, polyglycol polyamine condensates which contain alkyl group having 6–20 carbon atoms, adipic acid/dimethylaminohydroxypropyldiethylenetriamine copolymer ("Cartaretin", product of Sandoz AG, etc.), and besides, cationic polymers described in Japanese Patent Application Laid-Open Nos. 139734/1978, 53996/1983, 36407/1985 and 117821/1989. In the hair cosmetic compositions according to the present invention, these cationic polymers may preferably be incorporated in a proportion of 0.05–20.0%, particularly 0.1–10.0%.

In the hair cosmetic compositions according to the present invention, one or more of silicone derivatives such as dimethyl polysiloxane, methylphenyl polysiloxane, amino-modified silicones, carboxyl-modified silicones, fatty acid-modified silicones, alcohol-modified silicones, aliphatic alcohol-modified silicones, polyether-modified silicones, epoxy-modified silicones, fluorine-modified silicones, cyclic silicones and alkyl-modified silicones may be incorporated with a view toward making feel of the hair and skin to the touch still better. Such silicone derivative may be in the form of either a single substance or a latex composition obtained by emulsion polymerization according to the process described in Japanese Patent Publication No. 38609/1981. Of these silicone derivatives, dimethyl polysiloxane (polymerization degree: at least 500), polyether-modified silicones, amino-modified silicones, cyclic silicones and the like are particularly preferred because they make feel of the hair to the touch better. In the hair cosmetic compositions according to the present invention, the silicone derivatives may preferably be incorporated in a proportion of 0.01–20.0%, particularly 0.05–10.0%.

Further, the hair cosmetic compositions according to the present invention may also be added with optional ingredients, which are mixed routinely in hair cosmetic compositions, for example, good feel-imparting agents such as alkylamine oxides, fatty acid alkanolamides, squalane and lanolin; moisturizers such as propylene glycol, glycerol, diethylene glycol monoethyl ether, sorbitol and amide derivatives represented by the following general formula (7):

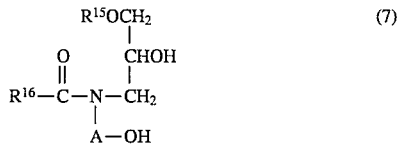

wherein $R^{15}$ a linear or branched, saturated or unsaturated hydrocarbon group having 10–26 carbon atoms, $R^{16}$ denotes a linear or branched, saturated or unsaturated hydrocarbon group having 9–25 carbon atoms, and A stands for —$(CH_2)_u$— in which u is an integer of 2–6; viscosity modifiers such as methyl cellulose, carboxyvinyl polymers, hydroxyethyl cellulose, polyoxyethylene glycol distearates and ethanol; pearl-like-hue-imparting agents; perfume bases; coloring matter; ultraviolet absorbents; antioxidants; disinfectants such as triclosan and triclocarban; antiphlogistics such as potassium glycyrrhetinate and tocopherol acetate; antidandruff agents such as zinc pyrithione and octopirox; antiseptics such as methylparaben and butylparaben; and other ingredients described in Encyclopedia of Shampoo Ingredients (Micelle Press, 1985) within limits not impeding the effects of the inventive hair cosmetic compositions.

The hair cosmetic compositions according to the present invention can be formulated in accordance with a method known per se in the art. They may preferably be adjusted to pH 2–10, in particular, pH 3–8 with a known acid or basic chemical which is used routinely in hair cosmetic compositions.

The hair cosmetic composition of the present invention are intended for all cosmetic compositions applied to the hair, including, for example, pre-shampooing agents, shampoos, hair rinses, hair conditioners, hair treatments, setting lotions, blow-styling lotions, hair sprays, styling foams, styling jellies, hair liquids, hair tonics, hair creams, first-package permanent wave compositions, second-package permanent wave compositions, permanent hair dye compositions and temporary hair dye compositions.

They can also be formulated in various forms such as an aqueous solution, an ethanol solution, an emulsion, a suspension, a gel, liquid crystals, solids and an aerosol according to their applications intended.

EXAMPLES

The present invention will hereinafter be described by the following examples. However, it should be borne in mind that this invention is not limited to and by these examples.

Example 1

Hair cosmetic compositions of their corresponding formulations shown in Tables 1 through 7 were prepared to conduct their performance evaluation tests. The results are shown in Tables 1 through 7.

Evaluation methods

Each about 20 g (about 15–20 cm long) of the hair of Japanese women, which had been subjected to hairdressing treatment such as cold permanent waving or bleaching, was bound up to shampoo it. Thereafter, 2 g of each of the hair cosmetic compositions was applied evenly to the hair thus shampooed and then rinsed out for 30 seconds with running water. The thus-treated hair was then towelled and dried further by a hair drier to evaluate the hair cosmetic composition in resilience, softness, oily feel, moistured feel and smoothness of the hair, the degree of occurrence of split hairs, and an effect of keeping the waves beautiful in accordance with the following standards, respectively.

(1) Resilience:
  A: The hair was very resilient.
  B: The hair was resilient.
  C: It was a toss-up whether the hair was resilient or not.
  D: The hair was lacking in resilience.
(2) Softness:
  A: The hair was very soft.
  B: The hair was soft.
  C: It was a toss-up whether the hair was hard or soft.
  D: The hair was hard.
(3) Oily feel:
  A: The hair felt very little oily.
  B: The hair felt slightly oily.
  D: It was a toss-up whether the hair felt oily or not.
  D: The hair felt strongly oily.
(4) Moistured feel:
  A: The hair felt strongly moistured.
  B: The hair felt moistured.
  C: It was a toss-up whether the hair felt moistured or not.
  D: The hair did not feel moistured.
(5) Smoothness:
  A: The hair was very smooth.
  B: The hair was smooth.
  C: It was a toss-up whether the hair was smooth or not.
  D: The hair was not smooth.
(6) Degree of occurrence of split hairs:
  The same hair as that treated in the above-described manner was brushed by a fixed number of times. The degree of occurrence of split hairs was evaluated by comparing the hair after the brushing with the hair before the brushing in accordance with the following standard:
  A: An increase in split hairs was not recognized.
  B: An increase in split hairs was scarcely recognized.
  C: An increase in split hairs was somewhat recognized.
  D: A great increase in split hairs was recognized.
(7) Effect of keeping the waves beautiful:
  Each about 5 g (about 20–30 cm long) of the hair of Japanese women, which had not been once subjected to any hairdressing treatment such as cold permanent waving or bleaching, was bound up and subjected to cold permanent waving so as to have the hair waved. After the hair thus treated was wetted with hot water of about 40° C., 0.25 g or 0.5 g of each of the hair cosmetic compositions was applied evenly to the hair to treat it, and rinsed out with running water. After the thus-treated hair was air-dried, the waving degree of the hair was evaluated in accordance with the following standard:
  A: The waves were kept very beautiful.
  B: The waves were kept beautiful.
  C: The waves were kept though not beautiful.
  D: The waves came out.
(8) Remaining rate of lipids:
  Each about 1 g of the hair of Japanese women, which had been subjected to hairdressing treatment such as cold permanent waving or bleaching, was bound up to shampoo it. Thereafter, 5 g of each of the hair cosmetic compositions was applied evenly to the hair thus shampooed, and the hair thus treated was left over for 4 hours at 60° C. The hair was then rinsed for 30 seconds with running water, shampooed, and then dried by a hair drier. The hair thus dried was treated by the Downing method, and lipids were determined by GC to evaluate the hair cosmetic composition in remaining rate of lipids in accordance with the following standard:

A: The remaining rate of lipids exceeded 5,000 μg/g (hair).

B: The remaining rate of lipids was 1,000–5,000 μg/g (hair).

C: The remaining rate of lipids was less than 1,000 μg/g (hair).

TABLE 1

| Ingredient (%) | Inventive composition | | | | | | |
|---|---|---|---|---|---|---|---|
| | 1 | 2 | 3 | 4 | 5 | 6 | 7 |
| Sodium polyoxyethylene (2.5) lauryl sulfate | 20 | — | — | — | — | 20 | 20 |
| Triethanolamine polyoxyethylene (2.5) lauryl sulfate | — | 20 | — | — | — | — | — |
| Triethanolamine lauryl sulfate | — | — | 20 | — | — | — | — |
| Sodium α-olefinsulfonate* | — | — | — | 20 | — | — | — |
| Imidazoline type surfactant** | — | — | — | — | 20 | — | — |
| Lauric acid diethanolamide | 3 | 3 | 3 | 3 | 3 | 3 | 3 |
| Benzyl alcohol | 5 | 5 | 5 | 5 | 5 | 5 | 5 |
| N-(2-Decyl)tetradecyl-N,N,N-trimethylammonium*** chloride | 0.5 | 0.5 | 0.5 | 0.5 | 0.5 | 0.5 | — |
| Stearyltrimethylammonium chloride | — | — | — | — | — | — | 0.5 |
| 3-Nonyldodecanoic acid | 2 | 2 | 2 | 2 | 2 | — | — |
| Lauric acid | — | — | — | — | — | 2 | 2 |
| Purified water | ← | | | Balance | | | → |
| Resilience | A | A | A | A | A | B | B |
| Softness | A | A | A | A | A | B | B |
| Oily feel | A | A | A | A | A | A | A |
| Moistured feel | A | A | A | A | A | B | B |
| Smoothness | A | A | A | A | A | A | A |
| Degree of occurrence of split hairs | A | A | A | A | A | A | A |
| Effect of keeping the waves beautiful | A | A | A | A | A | A | A |

*: Sodium tetradecenesulfonate.
**: Miranol C2M conc. (sodium salt of secondary amide type imidazoline surfactant derived from coconut oil fatty acid; product of Miranol chemical Co.).
***: Synthesized from a Guerbet alcohol (NJCOL-240A, product of Shin Nihon Rika K.K.).

TABLE 2

| Ingredient (%) | Comparative composition | | | | |
|---|---|---|---|---|---|
| | 1 | 2 | 3 | 4 | 5 |
| Sodium polyoxyethylene (2.5) lauryl sulfate | 20 | 20 | 20 | 20 | 20 |
| Triethanolamine polyoxyethylene (2.5) lauryl sulfate | — | — | — | — | — |
| Triethanolamine lauryl sulfate | — | — | — | — | — |
| Sodium α-olefinsulfonate* | — | — | — | — | — |
| Imidazoline type surfactant** | — | — | — | — | — |
| Lauric acid diethanolamide | 3 | 3 | 3 | 3 | 3 |
| Benzyl alcohol | — | — | — | 5 | — |
| N-(2-Decyl)tetradecyl-N,N,N-trimethylammonium*** chloride | — | 0.5 | — | 0.5 | 0.5 |
| Stearyltrimethylammonium chloride | — | — | 0.5 | — | — |
| 3-Nonyldodecanoic acid | — | — | — | — | 2 |
| Lauric acid | — | — | — | — | — |
| Purified water | ← | | Balance | | → |
| Resilience | D | D | D | D | C |
| Softness | D | D | D | C | C |
| Oily feel | D | C | D | C | C |
| Moistured feel | C | C | C | D | D |
| Smoothness | D | C | C | C | C |
| Degree of occurrence of split hairs | D | D | D | D | C |
| Effect of keeping the waves beautiful | D | D | D | D | C |

*: Sodium tetradecenesulfonate.
**: Miranol C2M conc. (sodium salt of secondary amide type imidazoline surfactant derived from coconut oil fatty acid; product of Miranol chemical Co.).
***: Synthesized from a Guerbet alcohol (NJCOL-240A, product of Shin Nihon Rika K.K.).

TABLE 3

| Ingredient (%) | Inventive composition | | | | | | | | |
|---|---|---|---|---|---|---|---|---|---|
| | 8 | 9 | 10 | 11 | 12 | 13 | 14 | 15 | 16 |
| Stearyltrimethylammonium chloride | — | — | — | — | 2 | — | — | 1 | — |
| N-(2-Dodecyl)hexadecyl-N,N,N-trimethyl ammonium chloride | 2 | 2 | 2 | 2 | — | 2 | 2 | 1 | 2 |
| Benzyloxyethanol | 5 | 5 | 5 | — | 5 | 5 | 10 | 10 | 5 |
| Benzyl alcohol | — | — | — | 5 | — | — | — | — | — |
| Stearic acid | 7 | — | — | — | — | 5 | 5 | — | — |
| Behenic acid | — | 7 | — | 7 | 7 | 2 | 2 | 7 | 7 |
| 18-Methylicosanoic acid | — | — | 7 | — | — | — | — | — | — |
| Cetyl alcohol | — | — | — | — | — | — | — | — | 3 |

TABLE 3-continued

| Ingredient (%) | Inventive composition | | | | | | | | |
|---|---|---|---|---|---|---|---|---|---|
| | 8 | 9 | 10 | 11 | 12 | 13 | 14 | 15 | 16 |
| Glycerol | 10 | 10 | 10 | 10 | 10 | 10 | 10 | 10 | 10 |
| Hydroxyethyl cellulose | 0.5 | 0.5 | 0.5 | 0.5 | 0.5 | 0.5 | 0.5 | 0.5 | 0.5 |
| Purified water | ← | | | | Balance | | | | → |
| Resilience | A | A | A | A | A | A | A | A | A |
| Softness | A | A | A | A | B | B | A | A | A |
| Oily feel | B | A | A | A | B | B | A | B | B |
| Moistured feel | B | A | A | A | B | B | A | A | B |
| Smoothness | B | A | A | A | B | B | A | A | B |
| Degree of occurrence of split hairs | A | A | A | A | A | A | A | A | A |
| Effect of keeping the waves beautiful | A | A | A | A | A | A | A | A | A |

TABLE 4

| Ingredient (%) | Comparative composition | | | |
|---|---|---|---|---|
| | 6 | 7 | 8 | 9 |
| Stearyltrimethylammonium chloride | 2 | 2 | — | — |
| N-(2-Dodecyl)hexadecyl-N,N,N-trimethylammonium chloride | — | — | 2 | 2 |
| Benzyloxyethanol | — | — | — | 5 |
| Benzyl alcohol | — | — | — | — |
| Stearic acid | — | — | — | — |
| Behenic acid | — | 7 | 7 | — |
| 18-Methylicosanoic acid | — | — | — | — |
| Cetyl alcohol | 3 | — | — | 3 |
| Glycerol | 10 | 10 | 10 | 10 |
| Hydroxyethyl cellulose | 05 | 0.5 | 0.5 | 0.5 |
| Purified water | ← | Balance | | → |
| Resilience | D | C | C | D |
| Softness | D | B | B | A |
| Oily feel | D | C | B | B |
| Moistured feel | D | C | B | B |
| Smoothness | D | C | B | B |
| Degree of occurrence of split hairs | D | B | B | C |
| Effect of keeping the waves beautiful | D | B | B | D |

TABLE 5

| Ingredient (%) | Inventive composition | | | | |
|---|---|---|---|---|---|
| | 17 | 18 | 19 | 20 | 21 |
| Stearyltrimethylammonium chloride | — | — | — | — | — |
| N-(2-Dodecyl)hexadecyl-N,N,N-trimethylammonium chloride | 2 | 2 | 2 | 2 | 2 |
| Benzyl alcohol | 5 | 5 | 5 | 5 | — |
| Benzyloxyethanol | — | — | — | — | 5 |
| Stearic acid monoglyceride | — | — | — | 7 | — |
| Oleic acid monoglyceride | 7 | — | — | — | 7 |
| Behenic acid | — | 7 | — | — | — |
| 18-Methylicosanoic acid | — | — | 7 | — | — |
| Cetyl alcohol | — | — | — | — | — |
| Glycerol | 10 | 10 | 10 | 10 | 10 |
| Hydroxyethyl cellulose | 0.5 | 0.5 | 0.5 | 0.5 | 0.5 |
| Purified water | ← | | Balance | | → |
| Resilience | B | A | A | B | A |
| Softness | A | B | A | A | A |
| Oily feel | A | B | A | B | A |
| Moistured feel | A | A | A | B | A |
| Smoothness | A | B | A | B | A |
| Remaining rate of lipids | A | A | A | B | A |

TABLE 6

| Ingredient (%) | Inventive composition | | | | |
|---|---|---|---|---|---|
| | 22 | 23 | 24 | 25 | 26 |
| Stearyltrimethylammonium chloride | 2 | — | — | 1 | — |
| N-(2-Dodecyl)hexadecyl-N,N,N-trimethylammonium chloride | — | 2 | 2 | 1 | 2 |
| Benzyl alcohol | 5 | 5 | 5 | 10 | 5 |
| Benzyloxyethanol | — | — | — | — | — |
| Stearic acid monoglyceride | — | — | — | — | — |
| Oleic acid monoglyceride | 7 | 5 | 5 | 7 | 7 |
| Behenic acid | — | 2 | — | — | — |
| 18-Methylicosanoic acid | — | — | 2 | — | — |
| Cetyl alcohol | — | — | — | — | 3 |
| Glycerol | 10 | 10 | 10 | 10 | 10 |
| Hydroxyethyl cellulose | 0.5 | 0.5 | 0.5 | 0.5 | 0.5 |
| Purified water | ← | | Balance | | → |
| Resilience | B | A | A | B | A |
| Softness | A | A | A | A | B |
| Oily feel | B | A | A | B | B |
| Moistured feel | A | A | A | A | B |
| Smoothness | B | A | A | A | B |
| Remaining rate of lipids | A | A | A | A | A |

TABLE 7

| Ingredient (%) | Comparative composition | | | |
|---|---|---|---|---|
| | 10 | 11 | 12 | 13 |
| Stearyltrimethylammonium chloride | 2 | 2 | 2 | 2 |
| N-(2-Dodecyl)hexadecyl-N,N,N-trimethylammonium chloride | — | — | — | — |
| Benzyl alcohol | — | — | — | — |
| Benzyloxyethanol | — | — | — | — |
| Stearic acid monoglyceride | — | — | — | 7 |
| Oleic acid monoglyceride | — | 7 | — | — |
| Behenic acid | — | — | 7 | — |
| 18-Methylicosanoic acid | — | — | — | — |
| Cetyl alcohol | 7 | — | — | — |
| Glycerol | 10 | 10 | 10 | 10 |
| Hydroxyethyl cellulose | 0.5 | 0.5 | 0.5 | 0.5 |
| Purified water | ← | Balance | | → |
| Resilience | D | C | B | D |
| Softness | D | B | C | D |
| Oily feel | D | B | C | C |
| Moistured feel | D | B | B | C |
| Smoothness | D | B | C | C |
| Remaining rate of lipids | C | B | B | C |

Example 2

Hair rinse composition:

A hair rinse composition having the following formulation was prepared in accordance with the conventionally-known method.

| (Ingredient) | (%) |
| --- | --- |
| (1) N-(2-Decyl) tetradecyl-N,N,N-trimethyl-ammonium chloride | 0.5 |
| (2) Stearyltrimethylammonium chloride | 1.0 |
| (3) Phenetyl alcohol | 5.0 |
| (4) Lignoceric acid | 3.0 |
| (5) Cetostearyl alcohol | 2.0 |
| (6) Zinc pyrithione | 0.3 |
| (7) Methylparaben | 0.2 |
| (8) Perfume base | 0.4 |
| (9) Deionized water | Balance |
| Total | 100 |

Example 3

Styling lotion composition:

A styling lotion composition having the following formulation was prepared in accordance with the conventionally-known method.

| (Ingredient) | (%) |
| --- | --- |
| (1) N-(2-Dodecyl)hexadecyl-N,N,N-trimethyl-ammonium chloride | 0.7 |
| (2) Polyethylene glycol | 1.5 |
| (3) Phenoxyethanol | 8.0 |
| (4) 2-Isoheptylisoundecanoic acid | 0.5 |
| (5) Liquid acrylic resin/liquid alkanolamine | 5.0 |
| (6) Methacrylic ester polymer | 1.0 |
| (7) Ethanol | 20.0 |
| (8) Perfume base | 0.4 |
| (9) Water | balance |
| Total | 100 |

Example 4

Hair conditioning foam composition:

A hair conditioning foam composition having the following formulation was prepared in accordance with the conventionally-known method.

| (Ingredient) | (%) |
| --- | --- |
| (1) N-(2-Decyl)tetradecyl-N,N,N-trimethyl-ammonium chloride | 0.5 |
| (2) Octyldodecyl myristate | 1.0 |
| (3) Dipropylene glycol | 1.0 |
| (4) 2-Benzyloxyethanol | 5.0 |
| (5) Heneicosanoic acid | 0.5 |
| (6) Glycerol | 2.5 |
| (7) Liquid paraffin | 2.5 |
| (8) Pentaerythritol.glyceryl isostearyl monoether | 0.5 |
| (9) Ethanol | 5.0 |
| (10) Methylparaben | 0.1 |
| (11) Perfume base | 0.1 |
| (12) Propellant (LPG) | 10.0 |
| (13) Water | Balance |
| Total | 100 |

Example 5

First-package permanent wave composition:

A first-package permanent wave composition having the following formulation was prepared in accordance with the conventionally-known method.

| (Ingredient) | (%) |
| --- | --- |
| (1) Ammonium thioglycolate | 6.0 |
| (2) Isostearic acid | 1.0 |
| (3) Aqueous ammonia | 3.0 |
| (4) Frost DS (disodium edetate) | 0.5 |
| (5) Benzyl alcohol | 10.0 |
| (6) N-(2-Decyl) tetradecyl-N,N,N-trimethyl-ammonium chloride | 2.0 |
| (7) Water | Balance |
| Total | 100 |

Example 6

Second-package permanent wave composition:

A second-package permanent wave composition having the following formulation was prepared in accordance with the conventionally-known method.

| (Ingredient) | (%) |
| --- | --- |
| (1) Sodium bromate | 8.0 |
| (2) N-(2-Decyl) tetradecyl-N,N,N-trimethyl-ammonium chloride | 2.0 |
| (3) Benzyl alcohol | 5.0 |
| (4) 2-Heptylundecanoic acid | 0.5 |
| (5) Water | Balance |
| Total | 100 |

Example 7

Shampoo composition:

A shampoo composition having the following formulation was prepared in accordance with the conventionally-known method.

| (Ingredient) | (%) |
| --- | --- |
| (1) N-Lauroyl-N'-carboxymethyl-N'-(2-hydroxyethyl)ethylenediamine TBA salt | 10.0 |
| (2) 18-Methyleicosanoic acid | 0.5 |
| (3) 2-Benzyloxyethanol | 5.0 |
| (4) Disodium polyoxyethylene (5) lauryl sulfosuccinate | 5.0 |
| (5) Lauric acid diethanolamide | 2.0 |
| (6) Coconut oil fatty acid amide propylbetaine | 2.0 |
| (7) Distearyldimethylammonium chloride | 0.1 |
| (8) Cationized cellulose (Polymer JR400, product of UCC) | 0.15 |
| (9) Perfume base | 0.5 |
| (10) Coloring matter | Proper amount |
| (11) Water | Balance |
| Total | 100 |

Example 8

Hair treatment composition:

A hair treatment composition having the following formulation was prepared in accordance with the conventionally-known method.

| (Ingredient) | (%) |
| --- | --- |
| (1) 2-Dodecylhexadecyltrimethylammonium chloride | 1.5 |
| (2) Stearyltrimethylammonium chloride | 2.0 |
| (3) Cetostearyl alcohol | 3.0 |
| (4) Oleic acid monoglyceride | 1.0 |
| (5) Benzyl alcohol | 5.0 |
| (6) Liquid paraffin | 3.0 |
| (7) Hydroxyethyl cellulose (1% aqueous solution, viscosity: 8,000 cp) | 0.5 |
| (8) Methylparaben | 0.2 |
| (9) Perfume base | 0.4 |
| (10) Water | Balance |
| Total | 100 |

Example 9

Hair conditioning composition:

A hair conditioning foam composition having the following formulation was prepared in accordance with the conventionally-known method.

| (Ingredient) | (%) |
| --- | --- |
| (1) Di(2-hexadecyl)dimethylammonium chloride | 0.5 |
| (2) Methylphenyl polysiloxane (300 CS) | 1.0 |
| (3) Dipropylene glycol | 1.0 |
| (4) 2-Benzyloxyethanol | 5.0 |
| (5) Stearic acid monoglyceride | 1.0 |
| (6) Glycerol | 2.5 |
| (7) Liquid paraffin | 2.5 |
| (8) Ethanol | 5.0 |
| (9) Methylparaben | 0.1 |
| (10) Perfume base | 0.1 |
| (11) LPG (4.0 kg/cm$^2$ · G, 20° C.) | 10.0 |
| (12) Water | Balance |
| Total | 100 |

INDUSTRIAL APPLICABILITY

The hair cosmetic compositions according to the present invention have neither sticky nor oily feel to the touch, are excellent in hair-conditioning effects of, for example, giving users a moistured feel of the hair and imparting softness and smoothness to the hair, give resilience to the hair and are superb in effects of preventing damage to the hair and of keeping the waves or curls of the hair beautiful.

We claim:

1. A hair cosmetic composition comprising:
   (a) at least one compound selected from the group consisting of fatty acids containing a linear or branched alkyl or alkenyl group having 18–25 carbon atoms, salts of fatty acids containing a linear or branched alkyl or alkenyl group having 18–25 carbons and fatty acid esters formed from fatty acids containing a linear or branched alkyl or alkenyl group having 18–25 carbon atoms and a polyhydric alcohol;
   (b) at least one aromatic alcohol of formula (1):

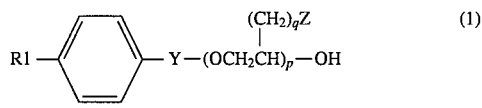

wherein
   $R^1$ is a hydrogen atom, a methyl group or methoxy group;
   Y is a single bond or a linear or branched alkylene or alkenylene group having 1–3 carbon atoms;
   Z is a hydrogen atom or a hydroxyl group; and
   p and q stand individually for a number of 0–5; and
   (c) at least one quaternary ammonium salt cationic surfactant, wherein the components (a), (b) and (c) are contained in proportions of 0.5–10 wt. %, 1–30 wt % and 0.2–10 wt %, respectively, based on the weight of the hair cosmetic composition.

2. The hair cosmetic composition as claimed in claim 1, wherein the component (b) is selected from benzyl alcohol, cinnamyl alcohol, phenethyl alcohol, p-anisyl alcohol, p-methylbenzyl alcohol, phenoxyethanol and 2-benzyloxyethanol.

3. A hair cosmetic composition comprising:
   (a) at least one compound selected from the group consisting of fatty acids containing a linear or branched alkyl or alkenyl group having 18–25 carbon atoms, salts of fatty acids containing a linear or branched alkyl or alkenyl group having 18–25 carbons and fatty acid esters formed from fatty acids containing a linear or branched alkyl or alkenyl group having 18–25 carbon atoms and a polyhydric alcohol;
   (b) at least one aromatic alcohol of formula (1):

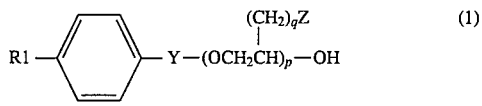

wherein
   $R^1$ is a hydrogen atom, a methyl group or methoxy group;
   Y is a single bond or a linear or branched alkylene or alkenylene group having 1–3 carbon atoms;
   Z is a hydrogen atom or a hydroxyl group; and
   p and q stand individually for a number of 0–5;
   (c) at least one quaternary ammonium salt cationic surfactant; and
   (d) a $C_{1-5}$ lower alcohol or $C_{2-5}$ lower polyol, wherein the components (a), (b), (c) and (d) are contained in proportions of 0.5–10 wt. %, 1–30% wt, 0.2–10 wt % and 0.1–50 wt. %, respectively, based on the weight of the hair cosmetic composition.

4. The hair cosmetic composition as claimed in claim 3, wherein the component (b) is selected from benzyl alcohol, cinnamyl alcohol, phenethyl alcohol, p-anisyl alcohol, p-methylbenzyl alcohol, phenoxyethanol and 2-benzyloxyethanol.

5. The hair cosmetic composition as claimed in claim 3, wherein the component (d) is selected from ethanol, isopropanol, n-propanol, n-butanol, isobutanol, ethylene glycol, propylene glycol, 1,3-butanediol and glycerol.

* * * * *